United States Patent [19]

Satoh et al.

[11] Patent Number: 5,354,434
[45] Date of Patent: Oct. 11, 1994

[54] METHOD FOR REGENERATING TETRAALKYLAMMONIUM HYDROXIDE

[75] Inventors: Hitoshi Satoh, Okayama; Motoko Fukui, Tamano; Chisako Kawakami, Kurashiki, all of Japan

[73] Assignee: Chlorine Engineers Corp. Ltd., Tokyo, Japan

[21] Appl. No.: 168,277

[22] Filed: Dec. 15, 1993

Related U.S. Application Data

[63] Continuation-in-part of Ser. No. 912,541, Jul. 13, 1992, abandoned.

[30] Foreign Application Priority Data

Jul. 12, 1991 [JP] Japan .................................. 3-172831
Oct. 16, 1991 [JP] Japan .................................. 2-267677

[51] Int. Cl.$^5$ .................... C02F 1/461; C25B 1/00
[52] U.S. Cl. ............................ 204/72; 204/102; 204/131; 204/182.4
[58] Field of Search ............... 204/72, 102, 131, 182.4

[56] References Cited

U.S. PATENT DOCUMENTS

| | | | |
|---|---|---|---|
| 3,968,017 | 7/1976 | Canata et al. | 204/131 |
| 4,536,269 | 8/1985 | Chlanda et al. | 204/182.4 |
| 4,714,530 | 12/1987 | Hale et al. | 204/131 |
| 4,752,363 | 6/1988 | Buckley et al. | 204/98 |
| 4,917,781 | 4/1990 | Sharifian et al. | 204/72 |
| 5,089,096 | 2/1992 | Rijkhof et al. | 204/102 |

Primary Examiner—John Niebling
Assistant Examiner—Arun S. Phasge
Attorney, Agent, or Firm—Kuhn and Muller

[57] ABSTRACT

Waste solution of developer, used as developer for a positive type photo resist and containing tetraalkylammonium hydroxide is neutralized with carbon dioxide, and it is filtered through a separation membrane. After removing precipitates of insoluble organic substances, it is sent to an anode chamber of an electrolytic cell divided by a cation exchange membrane, and electrolysis is performed. Low grade organic compounds in aqueous solution of tetraalkylammonium hydroxide obtained from a cathode chamber of a first stage electrolytic cell are oxidized and decomposed and are then supplied to an anode chamber of the next stage electrolytic cell, and high purity tetraalkylammonium hydroxide aqueous solution is obtained from the cathode chamber. Or, the solution is sent to an anode chamber of a multi-chamber electrolytic cell, where a plurality of ion exchange membranes are furnished and an intermediate chamber is provided between the anode chamber and the cathode chamber, low grade organic substances in the intermediate chamber are oxidized and decomposed, and high purity tetraalkylammonium hydroxide aqueous solution is obtained from the cathode chamber through electrolysis.

4 Claims, 3 Drawing Sheets

METHOD FOR REGENERATING TETRAALKYLAMMONIUM HYDROXIDE

This application is a continution-in-part of application Ser. No. 07/912,541, filed Jul. 13, 1992, now abandoned.

BACKGROUND OF THE INVENTION

The present invention relates to a method for regenerating tetraalkylammonium hydroxide to be used as a developer in fine fabrication of circuit pattern and the like by photolithography in the manufacturing processes of integrated circuits such as LSIs or ultra LSIs or liquid crystal display units.

Semiconductor integrated circuits such as ICs, LSIs, ultra LSIs, etc. are produced as follows: Photo resist is coated on a substrate such as silicon wafer, and a desired pattern is put on it by exposure using a stepper. Then, photolithography process such as developing, etching, etc. are repeated. Thin film transistor (TFT) for liquid crystal display unit is also manufactured by photolithography process on a glass substrate.

Photo resist is divided into a negative type resist, in which irradiated portion is insolubilized by exposure of circuit pattern, and a positive type resist, in which irradiated portion is solubilized.

As a typical positive type photo resist, novolak resin containing photosensitive substance such as o-diazonaphthoquinone is used. An example of a mixture of esterized o-diazonaphthoquinone sulfonic acid ester and m-cresol type novolak resin is given by the following chemical formula:

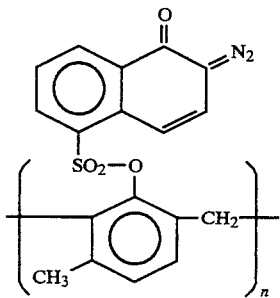

The o-diazonaphthoquinone sulfonyl group combined with novolak resin gives an effect to decrease solubility of novolak resin. When light such as ultraviolet ray is irradiated on o-diazonaphthoquinone, it is turned to ketene, and 3-indene-carboxylic acid is further generated under the presence of water:

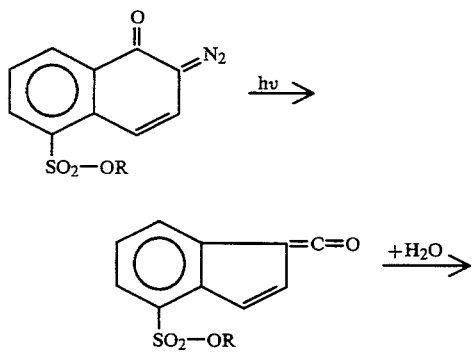

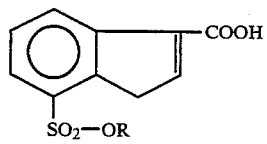

As the result, o-diazonaphthoquinone not only ceases to give effect as a dissolution inhibitor for novolak resin, but the alkali solubility is increased because acid is generated. Therefore, when a positive type photo resist with an exposed circuit pattern is developed by alkali solution, the exposed portion is dissolved by alkali solution, and a positive image is formed.

As alkali developer for the positive type resist, alkali carbonate, aqueous ammonia, tetramethylammonium hydroxide, etc. are used. With the increase of the devices with higher integration such as LSI, there are strong demands on the decrease of impurities in chemical agents to be used in the manufacturing process. Above all, there is strict restriction on intermingling of metal ions in the semiconductor manufacturing process. As the result, the developers containing tetramethylammonium hydroxide, which is an alkali solution containing no metal ion, as main component is now widely used in the process of photolithography.

Aqueous solution of hydroxide of tetraalkylammonium such as tetramethylammonium hydroxide used as a developer for the positive type photo resist had been disposed in the past as waste solution. This waste solution contains organic substances such as novolak resin, which is a major component of photo resist, and hydroxide of tetraalkylammonium contains nitrogen, which is turned to eutrophic component in water and causes contamination and deterioration of water quality. Thus, this has been disposed through various treatment procedures. With the increase in the quantity of developer used for the manufacture, the quantity of waste solution to be disposed also increased, and there have been urgent demands on the utilization of waste solution and on the decrease of the waste solution.

The present inventors have proposed a method for obtaining high purity tetraalkylammonium hydroxide from a cathode chamber in the Japanese Patent Application No. 2-408052 by introducing the waste solution into an anode chamber of an electrolytic cell, which is divided by a perfluorinated cation exchange membrane. According to this method, organic substances of novolak resin type in the waste solution, which is introduced into an anode chamber of an electrolytic cell, do not adversely affect the cation exchange membrane or move into the cathode chamber. But, when electrolysis is continued, concentration of organic substances such as novolak resin in the anode chamber increases, and the anode solution with increased organic substance concentration must be disposed, and it is impossible to completely regenerate and utilize tetraalkylammonium hydroxide in the waste solution.

In order to remove novolak resin and other organic substances from waste solution, it was attempted to apply membrane separation technique such as reverse osmosis method, ultrafiltration, etc. However, aqueous solution of hydroxide of tetraalkylammonium contained in the waste solution is strongly alkaline, and it is impossible to find a separation membrane, which is endurable to long-term use, and organic substances such as novolak resin in the waste solution cannot be separated by the application of the membrane separation technique.

It is an object of time present invention to provide tetraalkylammonium hydroxide, which has lower content of organic substances.

SUMMARY OF THE INVENTION

The present invention relates to a method for regenerating and utilizing waste solution of a developer containing tetraalkylammonium hydroxide which was used as a developer for a positive type photo resist as described above. The waste solution is neutralized and filtered through a separation membrane, insoluble organic precipitates containing novolak resin and others are removed, and aqueous solution of high purity tetraalkylammonium hydroxide is obtained from a cathode chamber by supplying the solution into an anode chamber of an electrolytic cell divided by cation exchange membrane and by performing electrolysis. The invention also relates to a method, by which said waste solution is neutralized with carbon dioxide and is filtered through separation filtration membrane and precision filter, and after insoluble organic precipitates containing novolak resin and others are removed, the filtrate is supplied to an anode chamber of an electrolytic cell divided by cation exchange membrane and electrolysis is performed, and it is collected from a cathode chamber through at least two cation exchange membranes.

Specifically, collection of the product from the anode chamber through two cation exchange membranes can be achieved by a method, in which a multi-stage electrolytic cell is furnished, aqueous solution of tetraalkylammonium hydroxide obtained in a cathode chamber of a first stage of an electrolytic cell is supplied to an anode chamber of the next stage of the electrolytic cell, and aqueous solution of high purity tetraalkylammonium hydroxide is obtained from the cathode chamber. Or, it can be achieved by a method, in which a multi-chamber electrolytic cell having a plurality of ion exchange membranes are furnished in an electrolytic cell and an intermediate chamber is furnished between the anode chamber and cathode chamber, the solution is supplied to the anode chamber, and aqueous solution of high purity tetraalkylammonium hydroxide is obtained from the cathode chamber.

Further, to increase removal ratio of low grade organic substances, aqueous solution of tetraalkylammonium hydroxide containing low grade organic compounds, passing through a first cation exchange membrane, is oxidized to decrease the content of low grade organic substances, and high purity tetraalkylammonium hydroxide containing very low content of low grade organic substances is obtained.

BRIEF DESCRIPTIONS OF THE DRAWINGS

DESCRIPTION OF THE PREFERRED EMBODIMENTS

Figure 1:
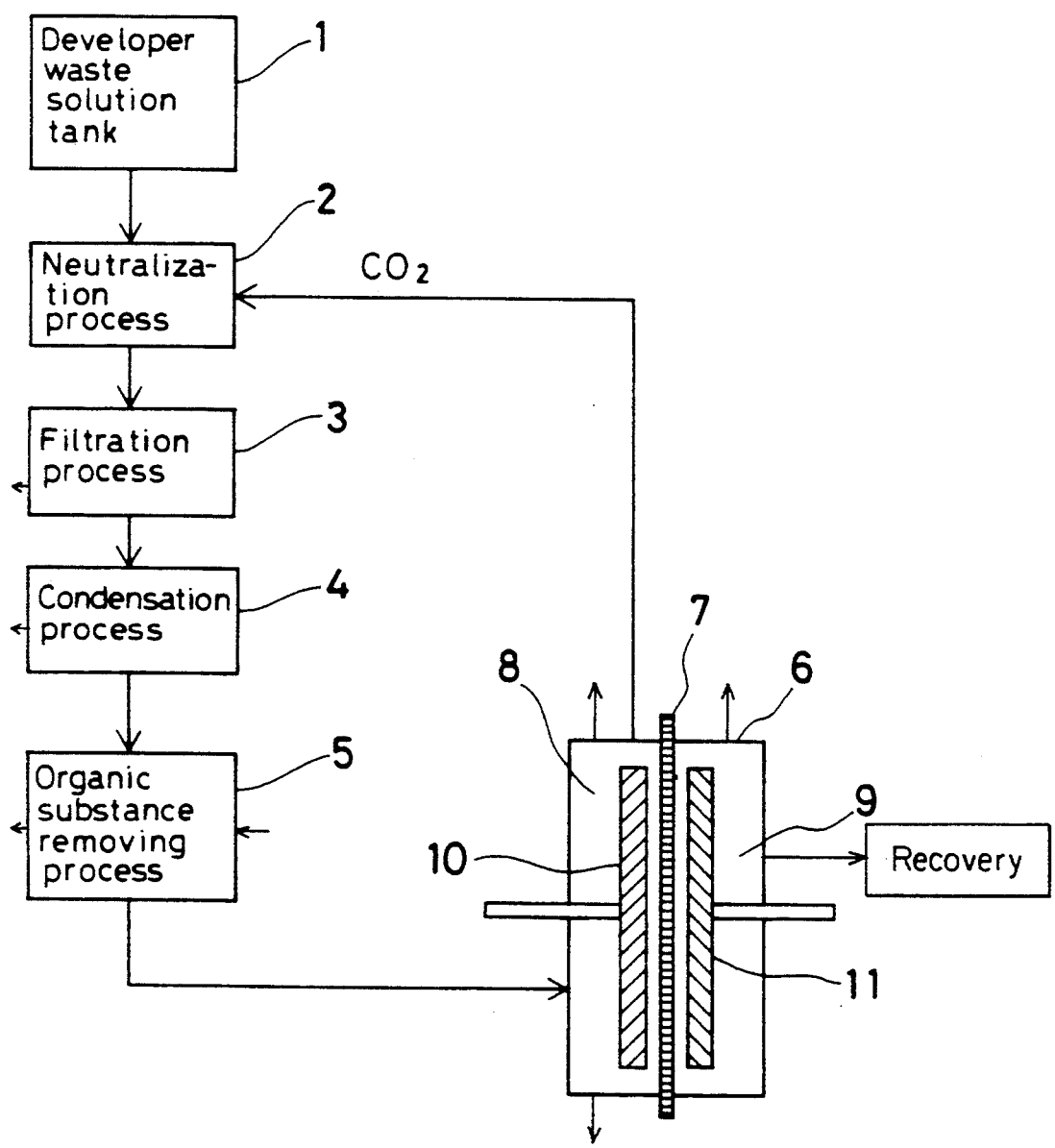
FIG. 1 shows a regeneration process of a waste solution of a developer.

Most types of materials used for fine fabrication in the manufacture of semiconductor devices such as LSIs are of very high purity, and very few quantity of impurities such as metal ions are normally intermingled in the process to use a developer. The impurities in the developer waste solution containing aqueous solution of tetramethylammonium hydroxide as main component are macromolecular organic substances of novolak resin type, which are the component of the positive type photo resist, or surface active agent, etc., and the intermingling of metal components such as alkali metal ions, sometimes causing problem in the manufacture of semiconductor devices, is negligible. Low grade organic substances used as solvents for photo resist are mostly evaporated in baking process of photo resist, and very few low grade organic substances are intermingled into the developer. Thus, unnecessary organic substances contained in the waste solution are mostly macromolecular organic substances such as novolak resin.

Since the photo resist such as novolak resin has carboxylic acid group and is dissolved in alkaline developer containing tetraalkylammonium hydroxide, when it is neutralized by adding acid, novolak resin is deposited as insoluble organic substance, and this can be separated by a method such as filtration from the solution. This makes it possible to reduce the content of unnecessary organic substance in the waste solution to very low value. When the waste solution thus treated is introduced into an anode chamber of an electrolytic cell partitioned by a perfluorinated cation exchange membrane and electrolyzed, very few organic substances are accumulated in the anode chamber, and the quantity of the waste solution to be disposed for eliminating the accumulated organic substances is reduced, and it is possible to efficiently collect tetraalkylammonium hydroxide.

For neutralization of the waste solution, it is possible to use various types of acids to neutralize alkali or various substances to generate acid when dissolved, but it is not desirable to use those substances such as anions including chlorine ion, sulfate ion, nitrate ion or the substances containing metal compounds which adversely affect when tetramethylammonium hydroxide is re-utilized in photolithography process. It is also not desirable to use organic acids, which adversely affect electrodes of the electrolytic cell or ion exchange membrane. Therefore, it is preferable to use carbonic acid or carbon dioxide, which does not generate undesirable anions. Further, carbonic acid increases the quantity of water in the waste solution, and it is more preferable to introduce gaseous carbon dioxide, which does not increase liquid quantity in the waste solution, into the waste solution for reaction.

When carbon dioxide is introduced into the waste solution, the following reaction occurs with tetraalkylammonium hydroxide, and bicarbonate or carbonate of tetraalkylammonium are generated, and the carbonate is further turned to bicarbonate.

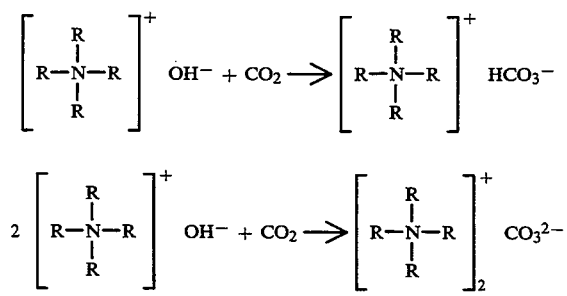

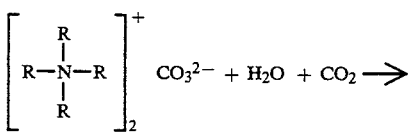

$$+ CO_3{}^{2-} + H_2O + CO_2 \longrightarrow$$

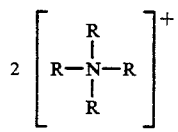 $HCO_3{}^-$ where

R represents an alkyl group.

As the result of neutralization, novolak resin dissolved in alkali is not any more dissolved in water and is deposited. After separating the deposited novolak resin through filtration membrane, the waste solution is introduced into the anode chamber of the electrolytic cell partitioned by a perfluorinated cation exchange membrane and electrolyzed, and the following chemical reaction occurs.

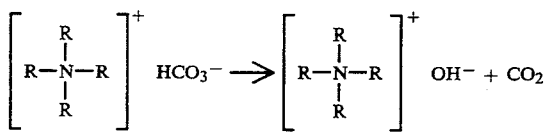

where

R represents an alkyl group.

In the anode chamber, carbon dioxide, oxygen, etc. are generated, and tetraalkylammonium ions move into the cathode chamber from the anode chamber through the cation exchange membrane, generating high purity tetraalkylammonium hydroxide.

Describing the method for regenerating tetraalkylammonium hydroxide of the present invention in connection of the drawings, the developer waste solution is sent from a waste solution tank 1 to a neutralization process 2 as shown in FIG. 1, where carbon dioxide gas is blown in, and pH value is adjusted. It is desirable to bring pH value as close to neutrality as possible in view of corrosion-resistant property of the filtration membrane in a filtration process 3. It is preferable to adjust pH value to 10 or lower, or more preferably, to about 8.

After removing organic substances in the filtration process, the waste solution is sent to a condensation process 4, where water is separated and the solution is condensed. Electrolysis can be performed without passing through the condensation process, but it is generally not very efficient to directly perform electrolysis because concentration of tetraalkylammonium compounds in the developer waste solution is as low as several weight %. Thus, it is preferable to increase electrolysis efficiency by condensing the solution to 5–60 weight %, or more preferably, to 15–40 weight %.

The neutralization process must be performed before the filtration process, while the condensation process may be performed after the filtration process or before the neutralization process.

The waste solution condensed in the condensation process is sent to an organic substance removing process 5 where soluble organic substances are decomposed. In case organic substances of ethylcellosolve type or surface active agent used as solvents for novolak resin are contained in large quantity, ion exchange membrane may be adversely affected, or bubbling may occur in the electrolytic cell by bubbles generated during electrolysis, or organic substances may be contained in tetraalkylammonium hydroxide obtained from the cathode chamber through cation exchange membrane. Thus, it is necessary to decrease the content of organic substances by decomposing them. To decompose organic substances, it is preferable to decompose by hydrogen peroxide, by ultraviolet ray, or by ozone.

The electrolytic cell 6 is divided into an anode chamber 8 and a cathode chamber 9 by a perfluorinated cation exchange membrane 7. As the cation exchange membrane of fluororesin type, ion exchange membrane of sulfonic acid type such as Nafion 324 (Dupont) may be used. As an anode 10, an electrode consisting of a corrosion-resistant base material with metal of platinum family or its oxide coated on it or an electrode such as magnetite having high corrosion-resistant property in oxidizing circumstances may be used. Depending upon the types of organic substances contained, a complex may be formed with coating of the electrode, and the coating may be deteriorated, and it is necessary to adequately select it according to the components of the organic substances contained. As the cathode 11, a metal resistant to alkali such as stainless steel, nickel, etc. may be used. Because carbon dioxide and oxygen are generated at the anode and gases such as hydrogen are generated at the cathode due to electrolytic reaction, it is preferable to use expanded metal, screen, perforated plate, etc. as base material for the anode or cathode.

When electrolysis is continuously performed by sending the developer waste solution to the anode chamber, the accumulation of organic substances at the anode chamber increases, and it is necessary to remove them. Compared with the conventional method, the quantity of the waste solution to be disposed is extensively reduced.

To adjust concentration of anode fluid and cathode fluid, an anode fluid circulation tank and a cathode fluid circulation tank may be furnished to circulate electrolytic solution between the anode chamber and the cathode chamber, and a pure water supply channel may be provided in the cathode fluid circulation route.

Mixture gas of carbon dioxide and oxygen generated at the anode chamber of the electrolytic cell may be used in the neutralization process for neutralizing alkalinity.

Figure 2:
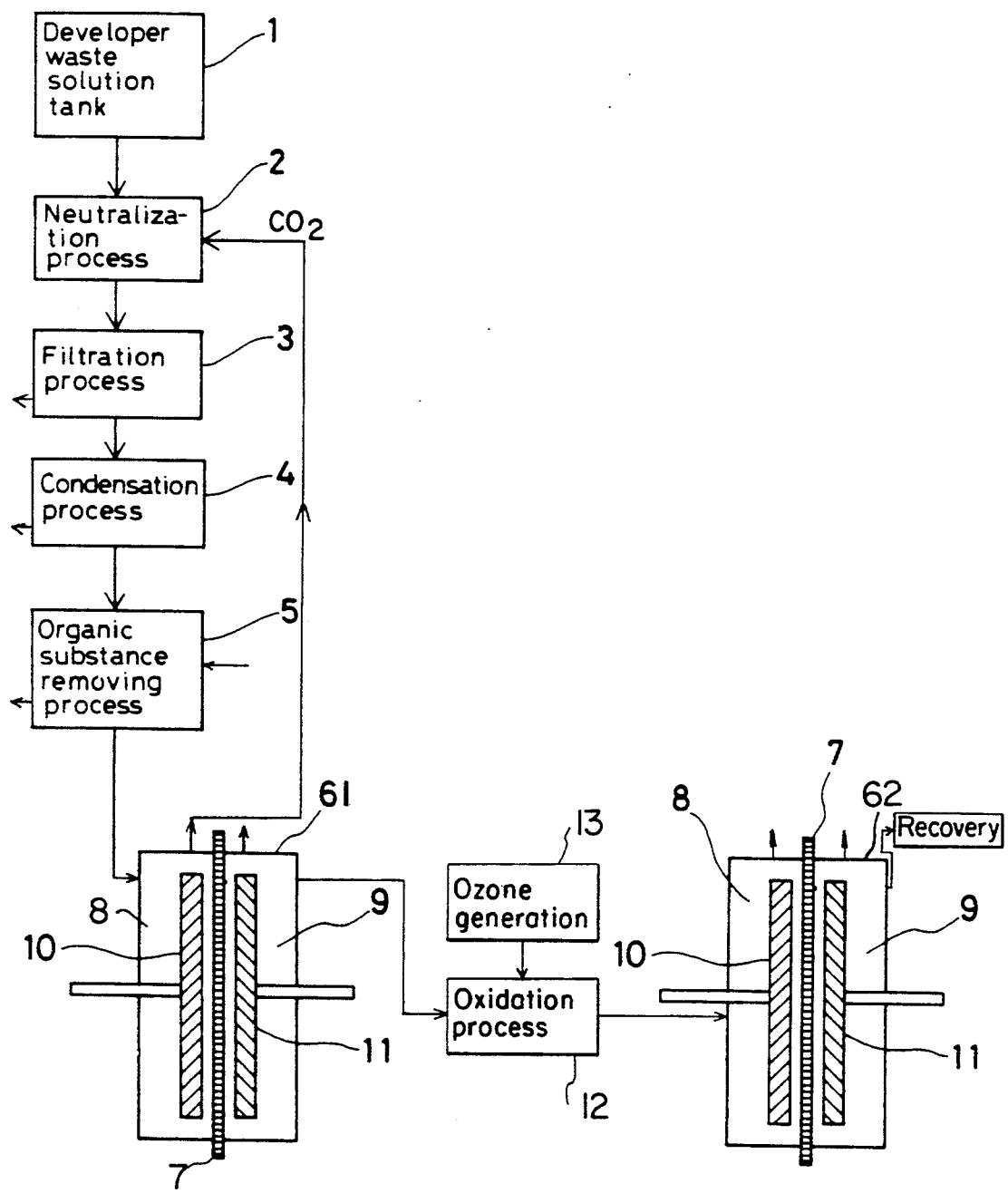
FIG. 2 is a diagram showing a method to regenerate the solution by two-stage electrolysis.

FIG. 2 represents a method for regenerating the solution through two-stage electrolysis.

The waste solution treated in an organic substance removing process is sent to an anode chamber of a first stage electrolytic cell 61 in a multi-stage electrolytic process where two-chamber type electrolytic cell is furnished in multiple stages.

The electrolytic cell is divided to an anode chamber 8 and a cathode chamber 9 by a perfluorinated cation exchange membrane 7. As the fluororesin type cation exchange membrane, solfonic acid type ion exchange membrane such as Nafion 324 (Dupont) may be used. Depending upon the types of organic substances contained, a complex may be formed with coating of the electrode, and the coating may be deteriorated, and it is necessary to adequately select it according to the components of the organic substances contained. As the cathode 11, a metal resistant to alkali such as stainless steel, nickel, etc. may be used. Because carbon dioxide and oxygen are generated at the anode and gases such as hydrogen are generated at the cathode due to electrolytic reaction, it is preferable to use expanded metal, screen, perforated plate, etc. as base material for the anode or cathode.

Tetraalkylammonium hydroxide obtained at the cathode chamber of the first stage electrolytic cell in the multi-stage electrolytic process may be directly supplied to the anode chamber of the electrolytic cell of the next stage, whereas the quantity of low grade organic substances contained in tetraalkylammonium hydroxide can be reduced by decomposing low grade organic substances passing through the cation exchange membrane in an oxidation process 12 before sending it to the electrolytic cell of the next stage and by sending it to the anode chamber of the electrolytic cell of the next stage.

To decompose low grade organic substances in the oxidation process 12, it is preferable to use a method by hydrogen peroxide, a method by ultraviolet ray, or a method by ozone. In particular, it is preferable to use a method to supply gas containing ozone from an ozone generator 13 into aqueous solution and to oxidize and decompose it because the quantity of aqueous solution to be treated is not increased.

As the result, aqueous solution of tetraalkylammonium hydroxide containing very few quantity of low grade organic substances can be obtained from the cathode chamber of the second stage electrolytic cell.

Figure 3:
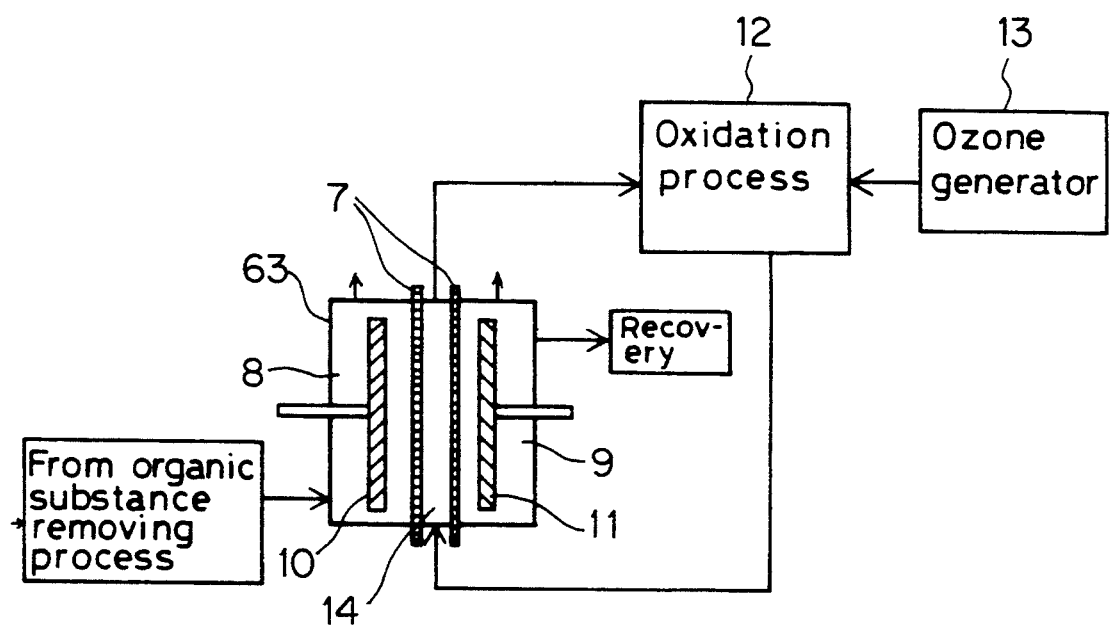
FIG. 3 represents a method with a multi-chamber electrolytic cell for electrolytic process.

FIG. 3 shows a method, in which the electrolysis process is carried out by a multi-chamber electrolytic cell.

In the multi-chamber electrolytic process, neutralization process and filtration are performed in the case of solution treatment in multi-stage electrolysis, and the solution is sent to an anode chamber of a 3-chamber electrolytic cell 63 divided by two cation exchange membranes. To remove low grade organic substances, which passed through the cation exchange membranes, electrolyte solution in an intermediate chamber is circulated to an oxidation process 12 to oxidize and decompose the organic substances.

From the cathode chamber of the 3-chamber electrolytic cell, aqueous solution of tetraalkylammonium hydroxide containing lower content of low grade organic substances can be obtained.

A two-stage example was shown for the multi-stage electrolytic process, and an example of a 3-chamber electrolytic cell was given for the multi-chamber electrolytic cells, while treatment can be made by multi-stage electrolytic process using 3 stages or more of a two-chamber electrolytic cell, or a multi-chamber electrolytic cell with three chambers of more may be used as the multi-chamber electrolytic cell.

The aqueous solution containing tetraalkylammonium hydroxide had been disposed as waste solution in the past after being used as developer for positive type photo resist in the photolithography process in the manufacture of semiconductor devices. According to the method of the present invention, this aqueous solution of tetraalkylammonium hydroxide is neutralized, organic substances soluble in alkali are removed, and the resultant solution is introduced into an anode chamber of an electrolytic cell and is electrolyzed. Thus, it is possible to decrease the quantity of the waste solution to be disposed and to obtain tetraalkylammonium hydroxide, which can be used again as a developer, from the cathode chamber.

Further, the regeneration method of this invention may be carried out at the site where the developer is used or may be performed at the place of intensive processing.

In the following, detailed description will be given on embodiments of the present invention:

EXAMPLE 1

Process to Prepare Neutralized Developer Waste Solution

To bottom surface of a 10-liter container lined with fluororesin on its inner surface, 50 g of novolak type positive photo resist (OFPR-800; Tokyo Ohka Industry Co., Ltd.) was lightly coated, and this was pre-baked in a hot air dryer at 90° C. for 120 minutes. Ethylcellosolve acetate and other volatile organic solvents in the resist were removed by evaporation, and after exposing to irradiation of ultraviolet ray for 60 seconds using a low voltage mercury lamp (450 W; Oak Manufacturing Co., Ltd.), 6 liters of high purity 5 weight % tetramethylammonium hydroxide aqueous solution were added to a stainless steel container, and photo resist was developed and dissolved.

Next, blowing high purity nitrogen into this developer waste solution, moisture was evaporated in a hot air dryer at 90° C., and the solution was condensed to $\frac{1}{3}$. After condensation, tetramethylammonium hydroxide in the developer waste solution was 14.8 weight % in concentration, 29,500 ppm in COD (Mn) value, and 14.0 in pH value.

Into the developer waste solution after condensation, high purity carbon dioxide was blown at a rate of 1.5 liters/min. for neutralization. Blowing of the carbon dioxide caused bubbling in the developer waste solution. When it was neutralized from pH 14 to pH 8, precipitates of novolak resin was generated in the waste solution.

Then, the developer waste solution after neutralization was filtered by precision filtration using an ultrafiltration membrane with molecular weight of 15,000. Thus, insoluble organic substances were filtered and separated to obtain neutralized waste solution. Tetramethylammonium hydrogencarbonate in the neutralized developer waste solution was 21 weight % in concentration, 6,000 ppm in COD (Mn) value, and 8.0 in pH value.

Electrolysis Process

As the electrolytic cell, a filter press type electrolytic cell having a pair of anode and cathode with electrode effective area of 0.2 dm$^2$ was used. Using Nafion 324 (Dupont), i.e. a perfluorinated sulfonic cation exchange membrane, the electrolytic cell was divided to an anode chamber and a cathode chamber. In the anode chamber of the electrolytic cell, an anode comprising a titanium electrode (Permelec Electrode Co., Ltd.) with coating of irridium oxide was provided, and a cathode made of nickel was provided in the cathode chamber. The neutralized developer waste solution was sent to the anode chamber at a rate of 5 liters/hour from a polyethylene container, and it was circulated between the anode chamber and the polyethylene container. In the cathode chamber, high purity 5.0 weight % tetramethylammonium hydroxide aqueous solution was filled in a 1.0 liter polyethylene container, and this was supplied by pump from the polyethylene container at a flow rate of 5 liters/hour. The overflow from the cathode chamber was circulated to the polyethylene container, and electrolysis was performed at electrolysis temperature of 30° C., constant current density of 10 A/dm$^2$, and electrolytic voltage of 9 to 11 V.

In the anode fluid, COD (Mn) value was 6,000 ppm when the electrolysis was started, but it was 6,500 ppm after 24 hours. COD (Mn) value of high purity 5.0 weight % tetramethylammonium hydroxide aqueous solution filled as the cathode fluid was less than 10 ppm when electrolysis was started, and 950 ppm at 24 hours after electrolysis was started.

The concentration of tetramethylammonium hydrogencarbonate in the anode fluid was 21.0 weight % when electrolysis was started, while it decreased to 10 weight % after 24 hours. In contrast, concentration of tetramethylammonium hydroxide in the cathode fluid increased after 24 hours from 5.0 weight % to 16.0 weight %. The concentration of impurities in 16.0 weight % tetramethylammonium hydroxide aqueous solution electrolyzed and collected as the cathode fluid was less than 10 ppb for each of Na, K, Fe, Cr, Ni, Mg, Ca, and Cu.

EXAMPLE 2

By the same procedure as in the Example 1, neutralized developer waste solution of 21 weight % in concentration, 6,000 ppm in COD (Mn) value, and 8 in pH value was prepared. To this waste solution, oxygen with ozone concentration of 79,000 ppm was supplied for 120 minutes at a rate of 2 liters/min. After oxidation process, 2 liters of the developer solution (composition analysis: tetramethylammonium hydrogencarbonate, 20.0 weight % in concentration, 5,400 ppm in COD (Mn) value) were circulated as anode fluid as in the Example 1, and electrolysis was performed under the same condition as in the Example 1. After 24 hours, 16.7 weight % tetramethylammonium hydroxide aqueous solution was obtained as the cathode fluid. COD (Mn) value was 840 ppm, and impurity concentration was less than 10 ppb for each of Na, K, Fe, Cr, Ni, Mg, Ca and Cu.

Vigorous bubbling occurred on anode side when electrolysis was performed by the procedure of the Example 1, but there was no problem of bubbling in ozone treatment of this Example.

EXAMPLE 3

The developer waste solution obtained by the neutralized developer waste solution preparation process of the Example 1 was electrolyzed using a two-stage electrolytic cell.

As the first stage electrolytic cell, a filter press type electrolytic cell having a pair of anode and cathode with electrode effective area of 0.2 dm$^2$ was used. Using Nation 324 (Dupont), i.e. a perfluorinated sulfonic cation exchange membrane, the electrolytic cell was divided to an anode chamber and a cathode chamber. In the anode chamber of the electrolytic cell, an anode comprising a titanium electrode (Permelec Electrode Co., Ltd.) with coating of iridium oxide provided, and a cathode made of nickel was provided in the cathode chamber. The neutralized developer waste solution was sent to the anode chamber at a rate of 5 liters/hour from a polyethylene container, and it was circulated between the anode chamber and the polyethylene container. In the cathode chamber, high purity 5.0 weight % tetramethylammonium hydroxide aqueous solution was filled in a 1.0 liter polyethylene container, and this was supplied by pump from the polyethylene container at a flow rate of 5 liters/hour. The overflow from the cathode chamber was circulated to the polyethylene container, and electrolysis was performed at electrolysis temperature of 30° C., constant current density of 10 A/dm$^2$, and electrolytic voltage of 8 to 10 V.

In the anode fluid, COD (Mn) value was 6,600 ppm when the electrolysis was started, but it was 8,300 ppm after 24 hours. COD (Mn) value of high purity 5.0 weight % tetramethylammonium hydroxide aqueous solution filled as the cathode fluid was less than 10 ppm when electrolysis was started, and 870 ppm at 24 hours after electrolysis was started.

The concentration of tetramethylammonium hydrogencarbonate in the anode fluid was 20.0 weight % when electrolysis was started, while it decreased to 3 weight % after 24 hours. In contrast, concentration of tetramethylammonium hydroxide in the cathode fluid increased after 24 hours from 5.0 weight % to 15.6 weight %.

When oxygen gas containing ozone at 70,000 ppm was blown into aqueous solution of tetraalkylammonium hydroxide generated in the cathode chamber of the first stage electrolysis process at a flow rate of 2 liters/min. for 2 hours, the concentration of tetraalkylammonium hydroxide was turned to 14.5 weight %, and COD (Mn) value decreased to 650 ppm.

Further, from a polyethylene container, which was filled with 2 liters of tetraalkylammonium hydroxide after oxidation process, the solution was circulated to the anode chamber of the electrolytic cell of the same structure as the first stage at a flow rate of 5 liters/hour. One liter of high purity 5.0 weight % tetraalkylammonium hydroxide aqueous solution was filled into a polyethylene container, and the overflow from the cathode fluid was circulated to the polyethylene container. Then, electrolysis was performed at electrolysis temperature of 30° C., constant current density of 10 A/dm$^2$, and electrolysis voltage of 8 to 10 V.

COD (Mn) value of the anode fluid was turned to 830 ppm at 24 hours after electrolysis was started, while COD (Mn) value of the cathode fluid was less than 10 ppm.

On the other hand, the concentration of tetraalkylammonium hydroxide decreased to 5 weight %, while the concentration of tetraalkylammonium hydroxide in the cathode fluid increased to 16.7 weight %.

In 16.7 weight % tetramethylammonium hydroxide aqueous solution collected as cathode fluid by electrolysis, the concentration of impurities was less than 10 ppb for each of Na, K, Fe, Cr, Ni, Mg, Ca, and Cu.

EXAMPLE 4

An electrolytic cell was divided by the same two cation exchange membranes as in the Example 3 to an anode chamber, an intermediate chamber and a cathode chamber. The same anode as in the Example 1 was used in the anode chamber, and the same cathode as in the Example 3 was used in the cathode chamber. Thus, a 3-chamber type electrolytic cell was prepared.

By the same procedure as in the Example 3, neutralized developer waste solution was prepared, which contained tetramethylammonium hydrogencarbonate of 21 weight % in concentration, 6,000 ppm in COD (Mn) value, and 8 in pH value. Two liters of this waste solution was filled in a polyethylene container and was supplied to the anode chamber at a flow rate of 5 liters/hour and was circulated between the anode chamber and the polyethylene container by pump. To the intermediate chamber, high purity 5.0 weight % tetramethylammonium hydroxide aqueous solution was supplied at a flow rate of 5 liters/hour from a polyethylene container where 1 liter of the solution was filled. The overflow from the intermediate chamber was introduced into the polyethylene container and circulated between it and the polyethylene container. At 6 hours after electrolysis was started and at 2 hours before electrolysis was stopped, oxygen gas containing ozone of 70,000 ppm was blown into the fluid in the polyethylene container at a flow rate of 2 liters/min., and low grade organic substances moving from the anode chamber to the intermediate chamber was oxidized and decomposed.

In the cathode chamber, 1 liter of high purity 5.0 weight % tetramethylammonium hydroxide aqueous solution was filled in a polyethylene container, and it was supplied from the polyethylene container to the cathode chamber by pump at a flow rate of 5 liters/hour, and the overflow was circulated to the polyethylene container.

Electrolysis was performed at electrolysis temperature of 30° C., constant current density of 10 A/dm$^2$, and electrolysis voltage of 16–17 V.

When electrolysis was started, COD (Mn) value in the anode fluid was 6,500 ppm as organic substance content index, while it was turned to 6,960 ppm at 24 hours after electrolysis was started.

In high purity 5.0 weight % tetramethylammonium hydroxide aqueous solution filled as the intermediate fluid, COD (Mn) value was less than 10 ppm when electrolysis was started, and it was 806 ppm at 24 hours after electrolysis was started. In the high purity 5.0 weight % tetramethylammonium hydroxide aqueous solution filled as cathode fluid, COD (Mn) value was less than 10 ppm when electrolysis was started, and 15 ppm at 24 hours after electrolysis was started.

The concentration of tetramethylammonium hydrogencarbonate in the anode fluid when electrolysis was started was 19.5 weight %, while concentration decreased to 4 weight % after 24 hours. The concentration of tetramethylammonium hydroxide in the cathode fluid was 5.0 weight % when electrolysis was started, while it increased to 16.7 weight % after 24 hours.

In the tetramethylammonium hydroxide aqueous solution of 16.7 weight % collected as cathode fluid by electrolysis, the concentration of impurities was less than 10 ppb for each of Na, K, Fe, Cr, Ni, Mg, Ca, and Cu.

What we claim is:

1. A method for regenerating tetraalkylammonium hydroxide by electrolysis in accordance with the following steps, wherein an aqueous solution of used tetraalkylammonium compound containing organic substances as impurities is neutralized, and after removing insoluble components by a separation membrane, said solution is supplied to an anode chamber of a first stage electrolytic cell, and electrolysis is performed, and further wherein an aqueous solution of tetraylammonium hydroxide obtained in the cathode chamber of the first stage electrolytic cell is supplied to an oxidation process to decrease the content of organic substances as impurities, and said oxidized aqueous solution is then supplied to an anode chamber of a next stage electrolytic cell.

2. A method for regenerating tetraalkylammonium hydroxide by electrolysis according to claim 1, wherein the oxidation process comprises ozonization.

3. A method for regenerating tetraalkylammonium hydroxide by electrolysis in accordance with the following steps, wherein an aqueous solution of used tetraalkylammonium compound containing organic substances as impurities is neutralized, and after removing insoluble components by a separation membrane said solution is supplied to an anode chamber of a multi-chamber electrolytic cell divided by a plurality of cation exchange membranes, and electrolysis is performed, wherein electrolyte in an intermediate chamber of a multi-chamber electrolytic cell is removed from the electrolytic cell and treated in an oxidation process to decrease the content of the organic substances, and further said electrolyte is recycled to the intermediate chamber, and then an aqueous solution of regenerated tetraalkylammonium hydroxide is obtained.

4. A method for regenerating tetraalkylammonium hydroxide by electrolysis according to claim 3, wherein the oxidation process comprises ozonization.

* * * * *